(12) United States Patent
Munekata et al.

(10) Patent No.: US 6,429,193 B1
(45) Date of Patent: Aug. 6, 2002

(54) CELL CHEMOTACTIC FACTOR (CCTF) ORIGINATING IN MAMMALIAN TOOTH PRICEMENT OR CEMENT, METHOD FOR PURIFYING THE SAME, AND NOVEL CONNECTIVE TISSUE ADHESION PROMOTERS CONTAINING THE SAME AS THE ACTIVE INGREDIENT

(75) Inventors: Masanobu Munekata, Sapporo; Kazuaki Nishimura, Sakai, both of (JP)

(73) Assignee: Kanebo, Ltd., Tokyo (JP)

( * ) Notice: Subject to any disclaimer, the term of this patent is extended or adjusted under 35 U.S.C. 154(b) by 0 days.

(21) Appl. No.: 09/486,020

(22) PCT Filed: Aug. 13, 1998

(86) PCT No.: PCT/JP98/03619

§ 371 (c)(1),
(2), (4) Date: Jun. 19, 2000

(87) PCT Pub. No.: WO99/09062

PCT Pub. Date: Feb. 25, 1999

(30) Foreign Application Priority Data

Aug. 19, 1997 (JP) .............................................. 9-238859

(51) Int. Cl.[7] .............................................. A62K 38/00
(52) U.S. Cl. .............................. 514/8; 424/49; 424/77; 424/152.1; 424/198.1; 424/477; 424/479; 424/524; 424/572
(58) Field of Search .......................... 424/49, 77, 152.1, 424/198.1, 477, 479, 524, 572; 514/8

(56) References Cited

U.S. PATENT DOCUMENTS 5,792,508 A * 8/1998 Kitamura et al. ............. 424/49

OTHER PUBLICATIONS

Yorimasa et al., Presence of Endogenous Chemotactic Factors for Periodontal Ligament Cells in Bovine Cementum and Bone. Oral Biol.,39(6): 529–533. Jun. 1994.*

Nishimura, K. et al. The Chemoattractive Potency of Periodontal Ligament, Cementum and Dentin for Human Gingival Fibroblasts. J. Periodont. Res., 24:146–148, 1989.*

Ogata. Y. et al.,Cementum, Root Dentin and Bone Extracts Stimulate Chemotactic Behavior in Cells from Periodontal Tissue.Comp. Biochem. Physiol., 116B(3):359–365, Mar. 1997.*

* cited by examiner

*Primary Examiner*—Leon B. Lankford, Jr.
*Assistant Examiner*—Kailash C. Srivastava
(74) *Attorney, Agent, or Firm*—Hogan & Hartson, L.L.P.

(57) ABSTRACT

A precementum- and/or cementum-derived chemotactic factor (CCTF) of a tooth of a Mammalian is characterized by a molecular weight measured by SDS-PAGE of 67000±1000. A process for purifying a precementum- and/or cementum-derived gingival fibroblast chemotactic factor (CCTF) of a Mammalian tooth includes eluting a protein mixture from precementum and/or cementum of a Mammalian tooth and purifying the precementum- and/or cementum-derived chemotactic factor (CCTF) from the eluted protein mixture by molecular weight fractionation, ion-exchange adsorption chromatography and hydroxyapatite adsorption chromatography. In the process for purifying the gingival fibroblast chemotactic factor (CCTF) the Mammalian is preferably a bovine.

3 Claims, 5 Drawing Sheets

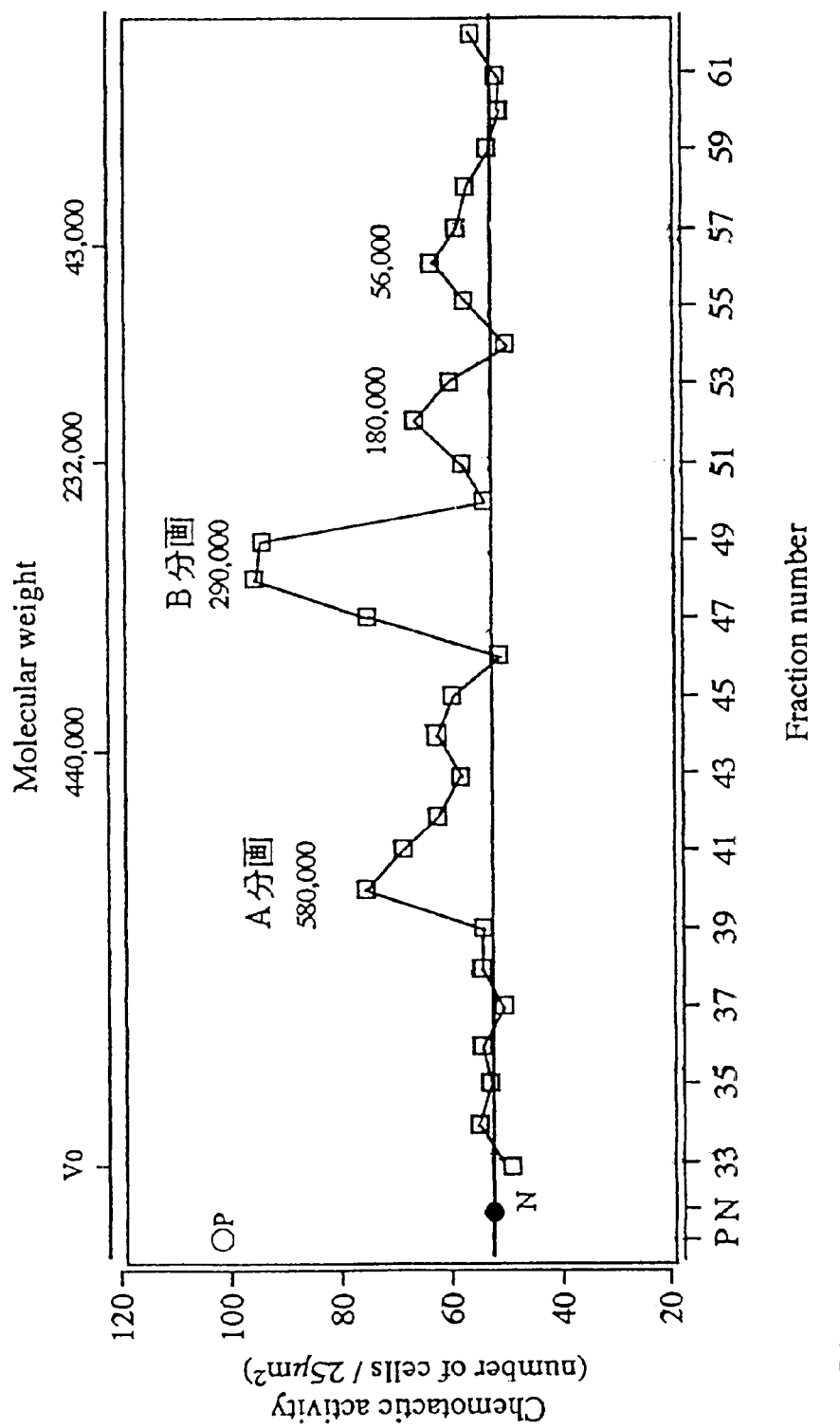
Fig. 1 Gel Filtration Chromatography
P: Positive control (DMEM medium containing 10% FBS)
N: Negative control (Only DMEM medium)

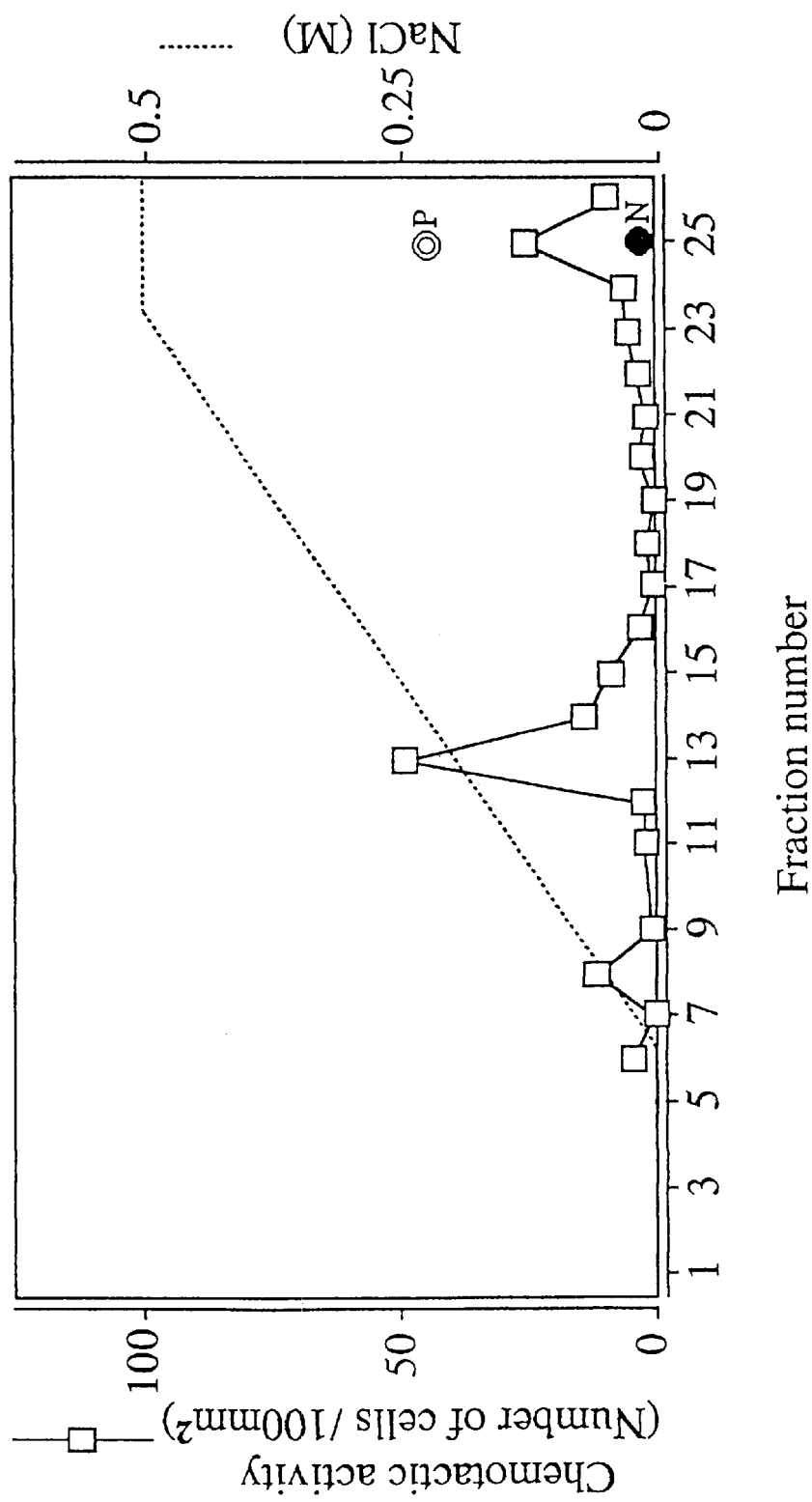
Fig. 2 DEAE-3SW ion exchange Chromatography
P(◎):Positive control (DMEM medium containing 10% FBS)
N(●):Negative control (Only DMEM medium)

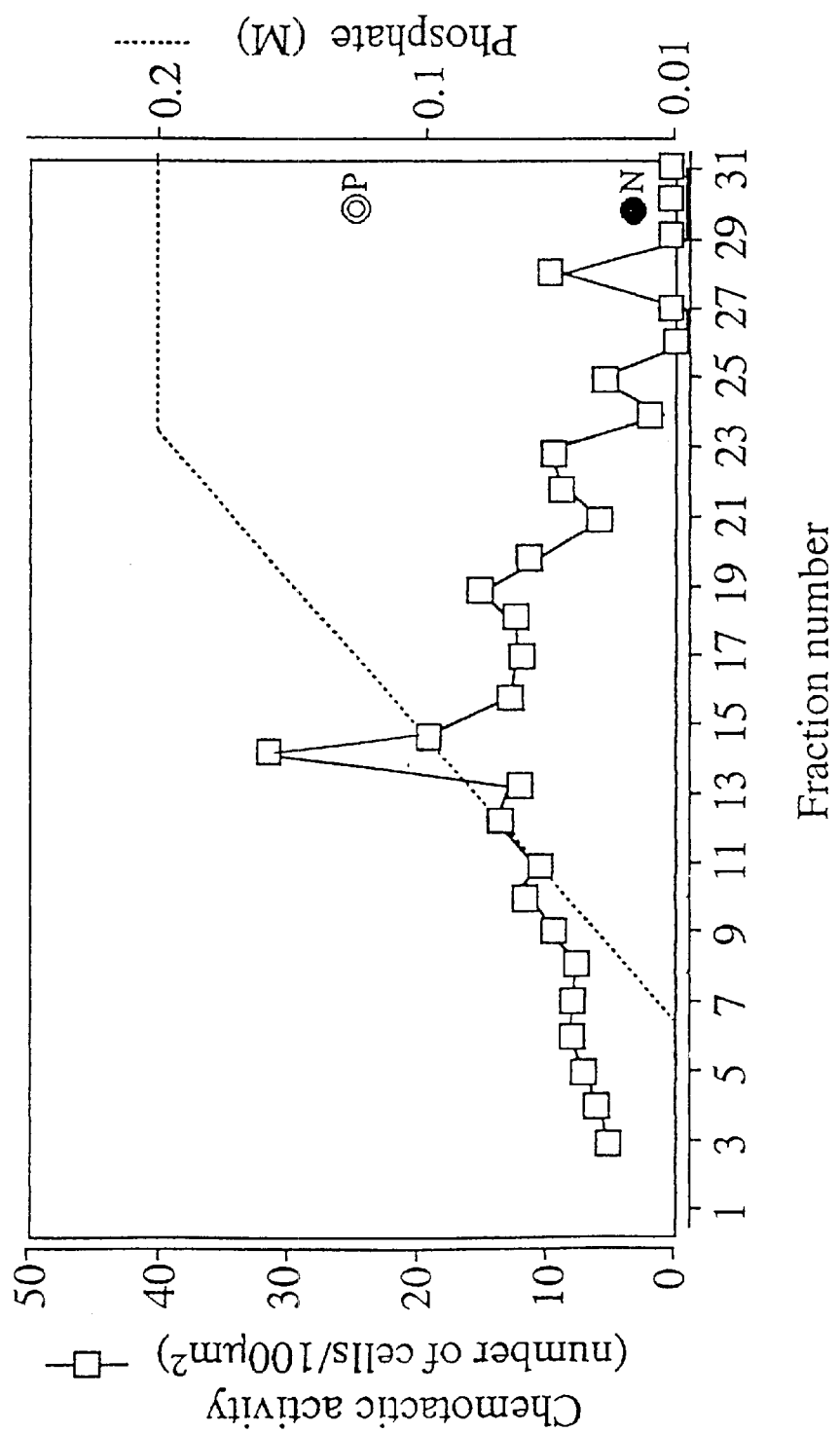
Fig. 3 Hydroxyapatite Chromatography
P : Positive control. (DMEM medium containing 10% FBS)
N : Negative control: (Only DMEM medium)

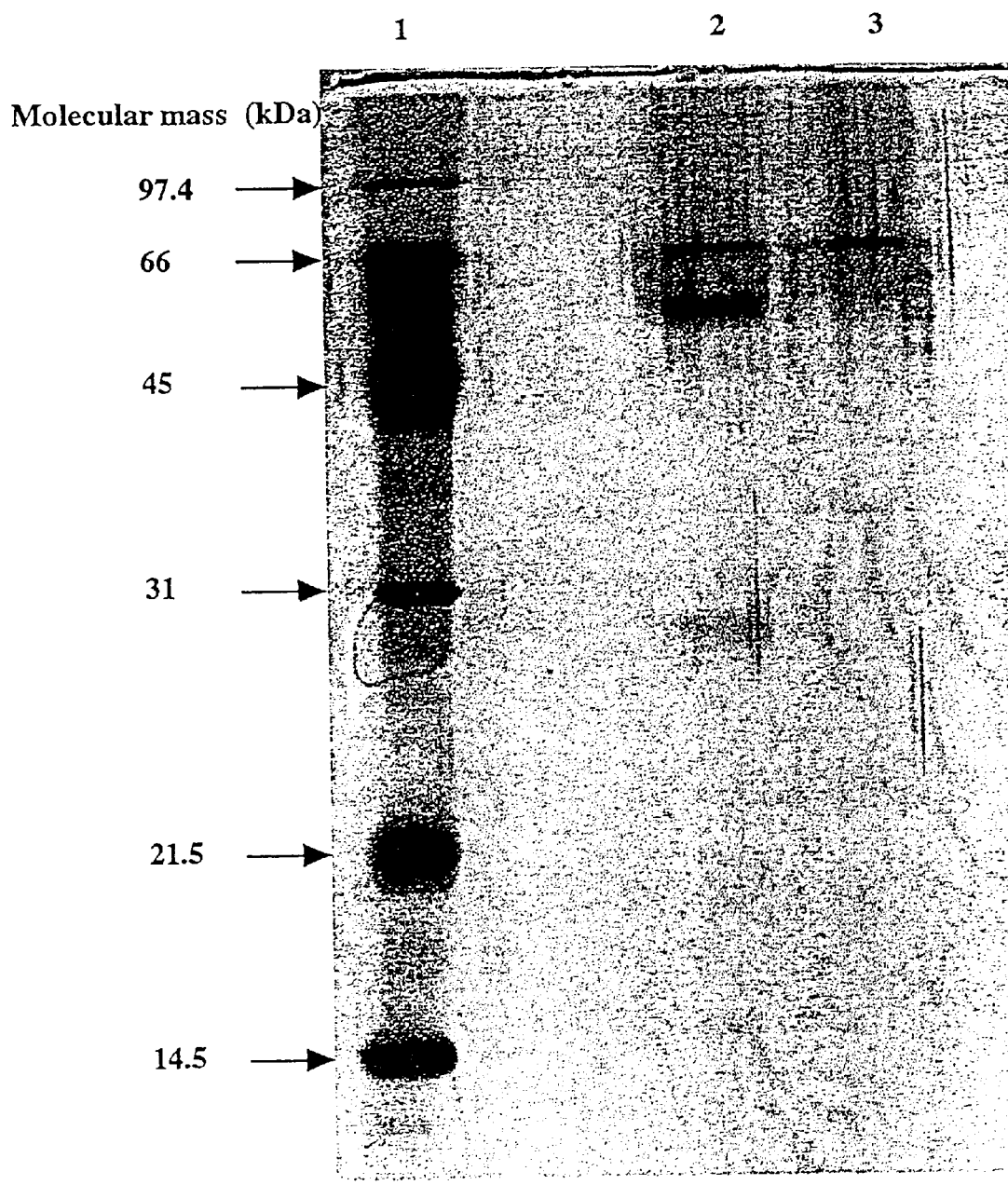
Fig. 4 SDS-Polyacrylamide Ggel Electrophoresis
lane 1 : marker
lane 2 : DEAE-3SW of chemotactic factor (Fr.13)
lane 3 : Hydroxy apatite of chemotactic factor (Fr.14)

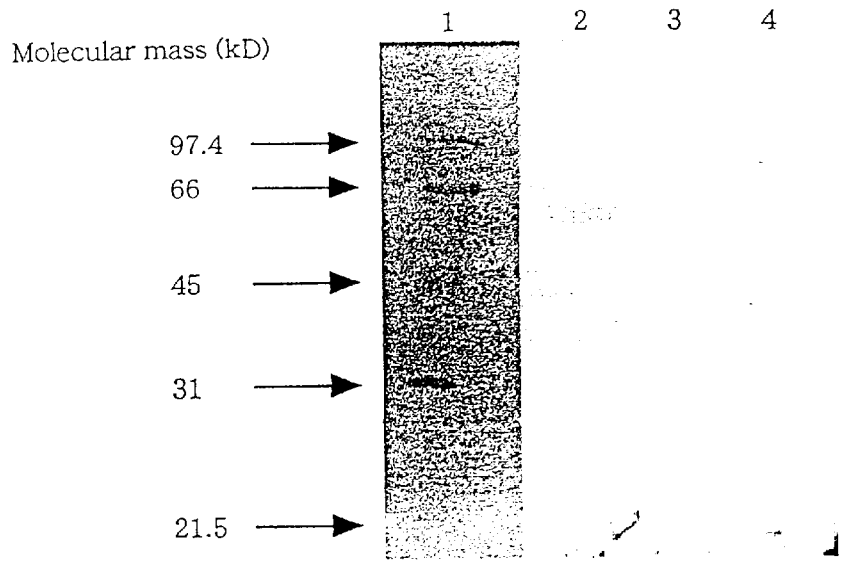
Fig. 5 Western blotting of CCTF using anti-BSP-II antibody
lane 1 : marker
lane 2 : BSP-II
lane 3 : 5×DEAE-3 SW Fr.13
lane 4 : 5×Hydroxyapatite Fr.14
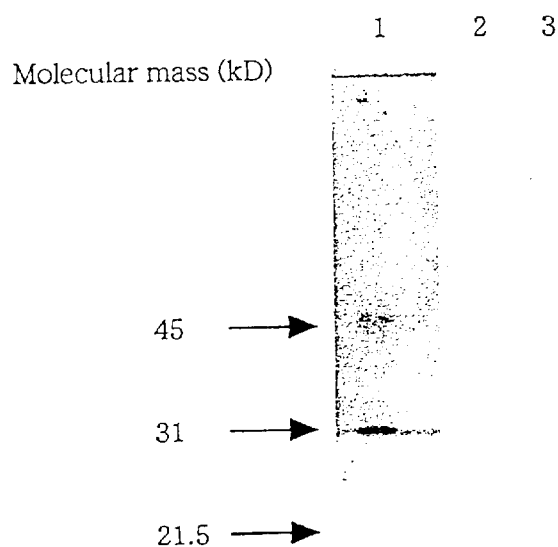
Fig. 6 Western blotting of CCTF using anti-BMP-2 antibody
lane 1 : marker
lane 2 : 5×DEAE-3 SW Fr.13
lane 3 : 5×Hydroxyapatite Fr.14

CELL CHEMOTACTIC FACTOR (CCTF) ORIGINATING IN MAMMALIAN TOOTH PRICEMENT OR CEMENT, METHOD FOR PURIFYING THE SAME, AND NOVEL CONNECTIVE TISSUE ADHESION PROMOTERS CONTAINING THE SAME AS THE ACTIVE INGREDIENT

TECHNICAL FIELD

The present invention relates to a precementum- and/or cementum-derived chemotactic factor (CCTF) of a tooth of Mammalia, a process for purifying the same, and a drug for accelerating adhesion of new connective tissue.

BACKGROUND ART

A periodontal disease is an inflammatory disease caused by breakage of supporting tissue of teeth (e.g. gum, periodontal ligament, alveolar bone, etc.) due to bacterial plaque (cluster of bacteria), and the periodontal disease and dental caries are referred to two typical diseases in the dental field.

In case of a severe periodontal disease, reconstruction of guided tissue by a surgical technique is required. Its purpose lies in not only removal of a periodontal pocket, but also restoring of an occluding function by regeneration of guided tissue broken due to the periodontal disease. A current typical technique is a gingival flap operation, however, regarding a curing style after operation, true adhesion between the tooth root and periodontal ligament (adhesion of new connective tissue) attended with neogenesis of cementum is limited to the root apex and ideal adhesion is not recognized in the other portion (epithelial adhesion).

Under these circumstances, a trial of various techniques has recently been made to positively obtain adhesion of new connective tissue. Among these techniques, a guided tissue regeneration technique (GTR technique) has attracted special interest. This GTR technique prevents or hinders the invasion of the defect portion of guided tissue, which has been curing, by gingival epithelium and gingival corium and thus allows the cells capable of attaching new connective tissue and forming an alveolar bone to grow into the defect portion, thereby regenerating guided tissue.

This technique is summarized as follows. First, a pocket formed by a periodontal disease is surgically removed and a gingival flap is detached, and then polluted cementum corresponding to the pocket is completely scraped. The tooth root surface is covered with a membrane and a gum is sutured on the membrane.

To regenerate sound guided tissue according to the above technique, it is necessary to induce migration, adhesion, growth and differentiation of gingival fibroblasts (hereinafter referred to as cells capable of adhering new connective tissue) to form newborn cementum around the periphery of a tooth root, thereby to obtain adhesion of new connective tissue, and to form an alveolar bone.

However, according to a therapy for a periodontal disease which is generally conducted at present, adhesion of new connective tissue and formation of an alveolar bone are insufficient.

An object of the present invention is to provide a substance which induces migration, adhesion, growth and differentiation of cells capable of adhering new connective tissue, thereby to accelerate adhesion of the new connective tissue between the tooth and gum (tooth root and periodontal ligament) and to provide a process for isolating and purifying the same, and to provide a drug for accelerating adhesion of new connective tissue, comprising the same as an active ingredient, which is used for restoring sound guided tissue with a periodontal disease.

DISCLOSURE OF THE INVENTION

An object of the present invention is attained by a precementum- and/or cementum-derived chemotactic factor (CCTF) of a tooth of Mammalia, characterized in that a molecular weight measured by SDS-PAGE is 67000±1000.

An object of the present invention is also attained by a process for purifying a precementum- and/or cementum-derived chemotactic factor (CCTF) of a tooth of Mammalia, wherein a molecular weight measured by SDS-PAGE is 67000±1000, which comprises collecting precementum and/or cementum from an extracted tooth of Mammalia and immersing them in saline or collagenase-containing saline with stirring to obtain an eluted ingredient, and purifying the eluted ingredient by molecular weight fractionation, ion-exchange adsorption chromatography and hydroxyapatite adsorption chromatography.

An object of the present invention is also attained by a drug for accelerating adhesion of new connective tissue, comprising the precementum- and/or cementum-derived chemotactic factor (CCTF) as an active ingredient.

The present inventors have studied about already-known cell adhesion and cell growth factors to solve the above problems, but brought no good solution. Therefore, they have further studied and found that precementum and/or cementum of a tooth of Mammalia contains a substance which has a chemotactic activity and causes invasion, growth and differentiation of cells capable of adhering new connective tissue, thereby to attract the cells to connective tissue.

The present inventors have also found that a novel chemotactic factor (hereinafter referred to as CCTF) can be purified by immersing precementum and/or cementum collected from extracted a tooth of Mammalia in saline or collagenase-containing saline with stirring to obtain an eluted ingredient, and subjecting the eluted ingredient to molecular weight fractionation, ion-exchange adsorption chromatography and hydroxyapatite adsorption chromatography. Thus, the present invention has been completed.

They have also found a drug for accelerating adhesion of new connective tissue, comprising CCTF as an active ingredient, which is useful for restoring sound guided tissue with a periodontal disease.

BRIEF DESCRIPTION OF THE DRAWINGS

FIG. 1 is a graph showing an elution pattern obtained by subjecting to HPLC gel filtration chromatography, after preparative columns TSK.G3000 TSK.G4000 for extract of precementum and cementum with a 1% collagenase-containing saline (pH 7) were connected each other in series.

FIG. 2 is a graph showing an elution pattern obtained by subjecting to DEAE ion-exchange chromatography, after mixing chemotactic activity fractions obtained in FIG. 1, each having a molecular weight of 270,000 to 290,000, 580,000 and 630,000 or more and concentrating the mixture.

FIG. 3 is a graph showing an elution pattern obtained by subjecting to HPLC hydroxyapatite chromatography, after concentrating a chemotactic activity fraction (Fr. No. 13) obtained in FIG. 2 by desalination.

FIG. 4 is a diagram showing an elution pattern obtained by measuring a chemotactic activity fraction (Fr. No. 14) CCTF obtained in FIG. 3 by SDS-PAGE (silver-colored portion is a detected portion).

FIG. 5 is a diagram showing a pattern of western blotting of CCTF using anti-BSP-II antibody FIG. 6 is a diagram showing a pattern of western blotting of CCTF using anti-BMP-2 antibody.

BEST MODE FOR CARRYING OUT THE INVENTION

CCTF of the present invention is a glycoprotein whose molecular weight measured by SDS-PAGE is 67000±1000, which is obtained from precementum and/or cementum of a tooth of Mammalia. Also, CCTF has a chemotactic activity and has an action of accelerating formation of cells capable of adhering new connective tissue.

The fact that CCTF is not fibronectin (molecular weight: 450 Kd) and vitronectin (molecular weight: 76 Kd) as a chemotactic factor has been proved by the fact that the chemotactic activity of CCTF was not inhibited by an antibody against fibronectin and vitronectin.

It has also been proved by western blotting that CCTF differs from BSP-II (molecular weight: 33.6 Kd, molecular weight of one containing a sugar chain: about 60 Kd) obtained by cementum which takes part in adhesion of gum cells and BMP-2 (molecular weight: 30 Kd) which takes part in regeneration of alveolar bone.

It has also been known that TGF-β and PDGF (platelet-derived growth factor) take part in regeneration of bone, in addition to BSP-II and BMP-2. It has been found that CCTF is not TGF-β or PDGF because the chemotactic activity of CCTF is not inhibited by these antibodies, i.e. anti-TGF-β antibody and anti-PDGF antibody, thereby making it clear that there is no substance corresponding to cell adhesion factors and cell growth factors which have ever been reported.

To obtain CCTF of the present invention, teeth extracted from Mammalia are used. Among Mammalia, bovine teeth are preferably used because of large population (a lot of bovines are now breeding for the purpose of using for food), easy availability of teeth, and large amount of CCTF obtained from a tooth.

CCTF is purified in the following procedure.

After periodontal ligament fibers are removed from an extracted tooth by using a scaler, precementum and/or cementum are scraped by using a sharp scaler and dispersed in saline (pH 7.0±0.5) containing 0–5% collagenase (collagenase is not contained in case of using only precementum), and then a protein ingredient is eluted with stirring. An insoluble matter is removed from the eluate by centrifugal separation. The eluate is subjected to membrane filter filtration and the filtrate is subjected to molecular weight fractionation such as gel filtration or ultrafiltration to obtain a fraction having a molecular weight of 270,000 or more.

The fraction is washed with a 50±5 mM tris ethanolamine hydrochloride buffer by DEAE ion-exchange chromatography (after adsorbing on a resin at pH of 7.5±0.5), and then a fraction to be eluted with, a 50±5 mM tris ethanolamine hydrochloride buffer containing 0.2–0.3 M sodium chloride is collected and concentrated by desalination.

The concentrated solution is adsorbed on hydroxyapatite equilibrated with a 10±1 mM phosphate buffer (pH 6.6±0.3 mM) and, after washing with a 10±1 mM phosphate buffer (pH 6.6±0.3 mM), the fraction to be eluted with 80–110 mM phosphoric acid is collected.

The substance thus obtained exhibits a single band of 67±1 Kd by SDS-PAGE. The substance is a glycoprotein containing sugar chains having an amino acid composition of: Asp; 10.6±0.5%, Thr; 3.7±0.3%, Ser; 13.3±0.7%, Glu; 13.8±0.7%, Gly; 23.3±1.2%, Ala; 10.1±0.5%, Cys/2; 3.6±0.3%, Val; 6.7±0.3%, Ile; 3.8±0.3%, Leu; 7.3±0.4% and Lys; 3.8±0.3%. The isoelectric point is 6.5±0.5.

The glycoprotein thus obtained is a substance which has a chemotactic activity and also has an action of accelerating adhesion of new connective tissue.

When using CCTF thus obtained of the present invention as a drug for accelerating adhesion of new connective tissue, for example, those obtained by immersing a collagen membrane, a gelatin membrane or other biodegradable membrane with the drug are applied to the affected part. Alternatively, the drug is applied in the form of paint, or applied by subcutaneous injection.

Specific direction for use includes, for example, process of accelerating adhesion of new connective tissue after operation by inserting those, which are obtained by immersing a collagen membrane, a gelatin membrane or other biodegradable membrane with a chemotactic factor of the present invention, into space between the tooth root surface smoothened by scraping a pollutant and the gum when applied to the flap operation as a therapy for periodontal disease. Sound guided tissue can be restored by using CCTF in such a manner.

EXAMPLES

The following Examples further illustrate the present invention in detail.

Example 1

First, periodontal ligament fibers of forty bovine teeth extracted from butchered bovines were removed not remaining using a scaler. Then, cementum containing precementum was scraped using a sharp scaler and dispersed in 20 ml of saline (pH 7) containing 1% collagenase. After the dispersion was stirred using Voltex (Automatic Mixer S-100, manufactured by Taiteck Co.) for 10 minutes, a protein ingredient was eluted. Furthermore, the insoluble matter was removed by centrifugal separation at 3000 rpm for 5 minutes to obtain a supernatant. Then, the supernatant was filtrated through a membrane filter having a pore diameter of 0.22μ (Durapore, manufactured by Nippon Milli pore Co.) and the filtrate was concentrated to 4 ml (11 mg of a protein content measured by Bradford's process). Preparative columns TSK G3000 (2.15 cm in inner diameter×60 cm in length, manufactured by Toso Co.) and TSK G4000 (2.15 cm in inner diameter×30 cm in length, manufactured by Toso Co.) were connected each other in series, and then molecular weight fractionation was conducted by HPLC gel filtration chromatography.

Each 4.2 ml of a fraction was collected and active fraction was determined in accordance with chemotaxis assay [K W. Falk et al., Immunol. Methods, Vol. 33, 239–247 (1980)] using human gingival fibroblasts.

Specifically, a D-MEM (serum free) medium containing 10% of each molecular weight fraction was divided into bottom wells in the chamber at 25 μl of medium/well using a 96-well microchemotaxis chamber (Neuro Probe, Cabin John, MD, USA). Furthermore, a D-MEM (10% FBS) medium was used as a positive control, while a D-MEM (serum free) was used as a negative control. On the bottom chamber, a filter having a pore diameter of 8 μm, a rubber and a top chamber were placed and fixed in this sequence. The D-MEM medium containing human gingival fibroblasts of $5 \times 10^5$ cells/ml was divided into wells in the top chamber at 50 μl of medium/well. The chamber was incubated for 3 hours at 37° C. under 5% $CO_2$–95% air. After the completion of the incubation, cells were fixed and stained with a Diff-Quich staining solution (International Reagents & Co., Japan), washed with water and then air-dried. The number of cells which migrated to the lower surface of the membrane filter were counted. The number of cells in a high power field was counted for each well by visually observing using an optical microscope (objective lens; ×20) wherein a grid micrometer is inserted into an ocular lens (×10).

As a result, a chemotaxis activity was recognized at fractions 40 to 41 having a molecular weight of about 580,000 or more (hereinafter referred to as "faction A") and fractions 47 to 49 having a molecular weight of about 270,000 to 290,000 (hereinafter referred to as "faction B"). The results are shown in FIG. 1.

Fractions A and B did not exhibit activity corresponding to TGF-β or BSP-II, and they were not deactivated by treating at 60° C. for 30 minutes.

It has already been found by a preparatory experiment that fractions A and B exhibit the same molecular weight band by SDS-PAGE when purified by DEAE ion-exchange chromatography and hydroxyapatite chromatography. Therefore, they were combined, concentrated by ultrafiltration to 2 ml. Then, the concentrate was adsorbed on a DEAE ion-exchange resin (TSK, DEAE-3SW, manufactured by Toso Co.) at pH 7.5, subjected to DEAE ion-exchange chromatography (DEAE-3SW: 7.5 mm in inner diameter×7.5 cm in length, manufactured by Toso Co.), washed with a 50 mM tris ethanolamine hydrochloride buffer and eluted with a gradient of a 0–0.5 M sodium chloride-containing 50 mM tris ethanolamine hydrochloride buffer. Furthermore, each 1 ml of fraction was collected and the active fraction was determined by chemotaxis assay described above. As a result, the activity was recognized at the fraction eluted with a 3M sodium chloride-containing 50 mM tris ethanolamine buffer. The results are shown in FIG. 2.

Then, each active fraction was concentrated by desalination. The concentrated fraction was subjected to chromatography on hydroxyapatite equilibrated with a 10 mM phosphate buffer (pH 6.8) (10 m in inner diameter×10 cm in length, manufactured by Koken Co.), washed with a 10 mM phosphate buffer (pH 6.8) and eluted with a gradient of 0–200 mM phosphate. Furthermore, each 1.5 ml of fraction was collected and the active fraction was determined by chemotaxis assay. As a result, chemotaxis activity was recognized in the fraction eluted with 80–110 mM phosphate. The results are shown in FIG. 3.

The fraction was concentrated by desalination to obtain 700 ng of CCTF. CCTF thus obtained exhibited a single band of 67±1 Kd by SDS-PAGE. The results are shown in FIG. 4.

Furthermore, this band was not stained by western blotting using anti-BSP-II antibody and anti-BMP-2 antibody. Thus, it has been found that CCTF is a substance different from BSP-II and BMP-2 (see FIGS. 5 and 6).

CCTF thus obtained has an amino acid composition of: Asp; 10/6%, Thr; 3.7%, Ser; 13.3%, Glu; 13.8%, Gly; 23.3%, Ala; 10.1%, Cys/2;3.6%, Val; 6.7%, Ile; 3.8%, Leu; 7.3% and Lys; 3.8%, and was an glycoprotein containing sugar chains. The isoelectric point was 6.5±0.5.

Then, 4 ml of a 5% collagen solution (type I-A) was prepared. To the solution, 200 ng of CCTF was added. 0.4 ml of the mixture was divided into each well in a 24-well plate (a well: bottom area; 1.77 $cm^2$, height; 2 cm) and polymerized in an open system. After 30 minutes, $5 \times 10^4$ of human gingival fibroblasts were inoculated on the collagen gel and then cultured for 3 days at 37° C. in the presence of 5% carbon dioxide. A sample for electron microscopy was prepared, embedded in epon, and then stained with toluidine blue. The invasion distance into CCTF-containing collagen and the number of inoculated human gingival fibroblasts were determined by visually observing using an optical microscope.

Furthermore, the effect of non-addition, or addition of fibronectin, TGF-β PDGF, or CCTF and anti-vitronectin antibody was examined in the same manner as described above. The results are shown in Table 1.

TABLE 1

| No. | | Number of invaded cells | Invasion Distance (μm) |
|---|---|---|---|
| 1** | No addition | 3.6 | 62.1 |
| 2* | CCTF 200 ng | 8.3 | 136.4 |
| 3** | TGF-β 200 ng | 5.5 | 102.0 |
| 4** | Fibronectin 200 ng | 4.8 | 72.3 |
| 5** | PDGF 200 ng | 7.1 | 122.4 |
| 6* | CCTF (200 ng) + anti-vitronectin | 8.1 | 136.2 |

*: Nos. 2 and 6: Examples
**: Nos. 1, 3–5: Comparative Examples

As shown in Table 1, in case where CCTF are added, both of the number of invaded cells and invasion distance into collagen gel was significantly higher than in case of no addition or addition of fibronectin, TGF or PDGF. The action of CCTF was not inhibited by anti-vitronectin antibody.

Example 2

First, periodontal ligament fibers of forty bovine teeth extracted from butchered bovines were removed not remaining using a scaler. Then, cementum and precementum were scraped using a sharp scaler and dispersed in 20 ml of saline (pH 7) containing 1% collagenase. After the dispersion was stirred using Voltex (Automatic Mixer S-100, manufactured by Taiteck. Co.) for 10 minutes, a protein ingredient was eluted. Furthermore, an insoluble matter was removed by centrifugal separation at 3000 rpm for 5 minutes to obtain a supernatant. Then, the supernatant was filtrated through a membrane filter having a pore diameter of 0.45μ (Durapore, manufactured by Nippon Milli pore Co.) and the filtrate was concentrated to 4 ml using an ultrafiltration membrane having a fractionated molecular weight is 200,000.

Then, the concentrate was adsorbed on a DEAE ion-exchange resin (TSK, DEAE-3SW, manufactured by Toso Co.) at pH 7.5, subjected to DEAE ion-exchange chromatography (DEAE-3SW: 7.5 mm in inner diameter×7.5 cm in length, manufactured by Toso Co.) and eluted with a gradient of a 0–0.5 M sodium chloride-containing 50 mM tris ethanolamine hydrochloride buffer. The fraction eluted with a 0.2–0.3 M sodium chloride-containing 50 mM tris ethanolamine hydrochloride was collected and then concentrated by desalination.

The concentrated fraction was subjected to chromatography on hydroxyapatite equilibrated with a 10 mM phosphate buffer (pH 6.6) (10 mm in inner diameter×10 cm in length, manufactured by Koken Co.) and then eluted with a gradient of 0–200 mM phosphate. The fraction eluted with 80–110 mM phosphate was collected and concentrated by desalination to obtain 730 ng of CCTF. CCTF thus obtained exhibited a single band of 67±1 Kd by SDS-PAGE.

Furthermore, this band was not stained by western blotting using anti-BSP-II antibody and anti-BMP-2 antibody. Thus, it has been found that CCTF is a substance different from BSP-II and BMP-2.

Then, 10 ml of a 5% collagen solution (type I-A) was prepared and the solution was mixed with 600 ng of CCTF described above. The mixture was poured in a thick of 2 mm and freeze-dried to form a CCTFcontaining collagen membrane. This was subjected to sterilized by ultraviolet light for two hours immediately before use.

After gingival flap of left and right incisors and lateral incisors of an upper jaw of a monkey was exfoliated and tumbled on the side of a labellum, an alveolar bone was cut out toward the side of an apiculus by about 4 mm to expose a tooth root. The exposed tooth root was smoothened by scraping cementum on the surface. The exposed left tooth root face was covered with CCTF-containing collagen membrane, while the exposed right tooth root face was left as it was, and then the gingival flap was replaced and sutured. After operation, plaque control was applied everyday for three weeks until curing is recognized.

After three weeks, the animal was butchered, perfused and fixed. A tissue block was collected to prepare a paraffin section and then H-E staining was applied. Histological observation revealed that adhesion of new connective tissue has been recognized in the left one treated with CCTF-containing collagen. Formation of an alveolar bone has also been recognized. On the other hand, both of them has not been recognized in the right one.

Industrial Applicability

The invention of claim 1 provides CCTF which accelerates adhesion of new connective tissue by applying to the defect portion, thereby to restore sound guided tissue.

According to the purification process of the invention of claim 4, CCTF of the present invention can be efficiently extracted and purified.

According to the invention of claim 7, there can be provided a drug for accelerating adhesion of new connective tissue between the tooth and gum (tooth root and periodontal ligament).

What is claimed is:

1. A process for purifying a precementum- and/or cementum-derived gingival fibroblast chemotactic factor (CCTF) of a Mammalian tooth, which comprises eluting a protein mixture from precementum and/or cementum of a Mammalian tooth and purifying the precementum- and/or cementum-derived chemotactic factor (CCTF) from the eluted protein mixture by molecular weight fractionation, ion-exchange adsorption chromatography and hydroxyapatite adsorption chromatography.

2. The process for purifying the gingival fibroblast chemotactic factor (CCTF) of claim 4 further comprising the steps of:

(a) collecting precementum and/or cementum from an extracted Mammalian tooth and immersing them in saline or collagenase-containing saline with stirring, thereby to elute the protein mixture;

(b) removing an insoluble matter from the eluted protein mixture of step (a) by centrifugal separation and filtration, and subjecting the resulting filtrate to gel filtration or ultrafiltration to obtain a fraction having a molecular weight fraction of 270,000 or more;

(c) adsorbing the fraction obtained in step (b) on a DEAE ion-exchange resin, collecting a fraction eluted with a 0.2–0.3 mM sodium chloride-containing tris ethanolamine hydrochloride buffer, and concentrating the fraction by desalination; and (d) adsorbing the concentrated fraction obtained in step (c) on hydroxyapatite equilibrated with a phosphate buffer, and collecting a fraction eluted with 80–110 mM phosphoric acid.

3. The process for purifying the gingival fibroblast chemotactic factor (CCTF) according to claim 1 or 2, wherein the Mammalian is a bovine.

* * * * *